United States Patent
Peukert et al.

(10) Patent No.: US 6,949,754 B2
(45) Date of Patent: Sep. 27, 2005

(54) APPARATUS FOR MEASURING IN PARTICULAR LUMINESCENT AND/OR FLUORESCENT RADIATION

(75) Inventors: Michael Peukert, Straubenhardt (DE); Norbert Klaiber, Enzklösterle (DE); Berthold Breitkopf, Straubenhardt (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 197 days.

(21) Appl. No.: 10/206,824

(22) Filed: Jul. 29, 2002

(65) Prior Publication Data

US 2003/0042428 A1 Mar. 6, 2003

(30) Foreign Application Priority Data

Jul. 28, 2001 (DE) .......................................... 101 36 863

(51) Int. Cl.[7] .............................................. G01N 21/64
(52) U.S. Cl. ................... 250/458.1; 250/459.1; 250/461.1; 250/461.2
(58) Field of Search ........................ 250/458.1, 459.1, 250/461.1, 461.2

(56) References Cited

U.S. PATENT DOCUMENTS

| | | | | |
|---|---|---|---|---|
| 3,916,205 A | * | 10/1975 | Kleinerman | ............ 250/461.2 |
| 5,206,568 A | | 4/1993 | Björnson et al. | |
| 5,290,513 A | | 3/1994 | Berthold et al. | |
| 5,682,232 A | * | 10/1997 | Tajima et al. | ............... 356/246 |
| 6,057,114 A | | 5/2000 | Akong et al. | |
| 6,236,456 B1 | | 5/2001 | Giebeler et al. | |
| 6,488,892 B1 | * | 12/2002 | Burton et al. | ............. 422/82.05 |
| 6,603,537 B1 | * | 8/2003 | Dietz et al. | .................... 356/39 |
| 2002/0109841 A1 | * | 8/2002 | Gould et al. | ................. 356/318 |

FOREIGN PATENT DOCUMENTS

| | | |
|---|---|---|
| DE | 4123817 A1 | 1/1993 |
| DE | 197 04 732 A1 | 8/1998 |
| DE | 197 07 226 A1 | 8/1998 |
| EP | 0 803 724 A2 | 10/1997 |
| GB | 2 381 311 A | 4/2003 |
| WO | WO 01/04608 A1 | 1/2001 |
| WO | WO 01/63262 A1 | 8/2001 |

* cited by examiner

*Primary Examiner*—Daivd Porta
*Assistant Examiner*—Shun Lee
(74) *Attorney, Agent, or Firm*—Browdy and Neimark, PLLC

(57) ABSTRACT

An apparatus for selected measurement of, in particular, luminescent and/or fluorescent radiation has a plurality of measurement light paths (M1, M2, M3), which each have their own measuring devices optimized for the particular measurement mode. As a common device, a filter holder (5) is used, in which the detector and each of the measuring devices have access to each of the openings of the filter holder, and each of these openings can be equipped with an emissions filter that is expedient for the particular measurement mode involved. The result is an especially compact arrangement of a multipurpose measuring instrument with measurement properties that are largely equivalent to the measurement properties of special individual measuring instruments and that is also suitable in particular as an individual instrument for special luminescence measurements, such as BRET measurements.

17 Claims, 13 Drawing Sheets

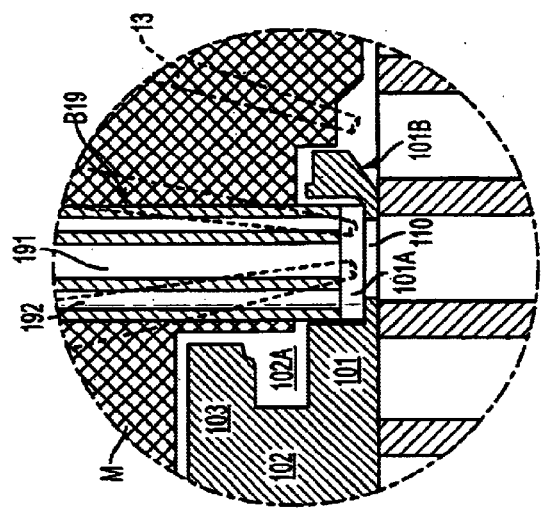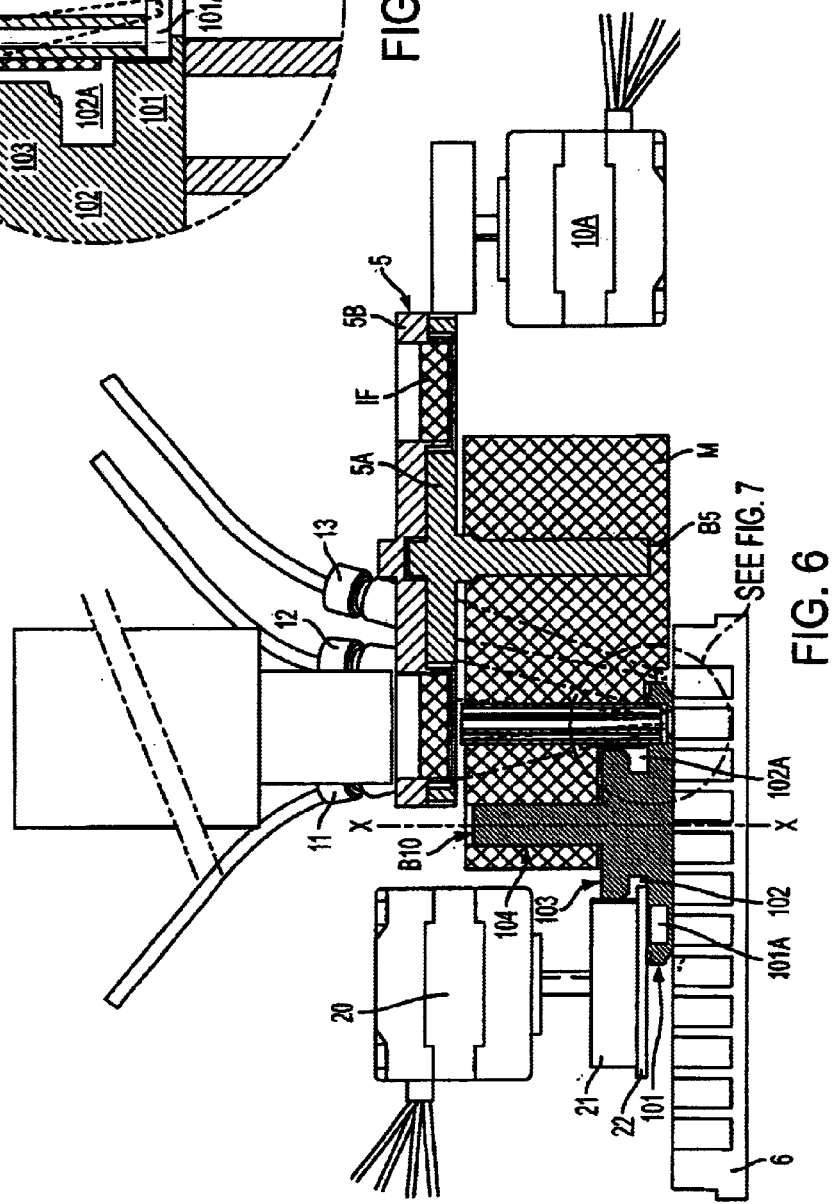

APPARATUS FOR MEASURING IN PARTICULAR LUMINESCENT AND/OR FLUORESCENT RADIATION

BACKGROUND OF THE INVENTION

Various producers of radiation measuring instruments using microtiter plates have changed over, because of decreasing budgets and a difficult cost structure for research, to instruments that can be used in multiple ways. The goal is to make a multipurpose instrument available to the customer for as many measuring methods as possible, in particular for measuring luminescence and fluorescence, so that it is unnecessary to procure a plurality of different individual instruments. Despite their higher price, compared to an instrument that is specialized for a particular measuring method, these multipurpose instruments are in strong demand. It is suggested that the customer by purchasing such a multipurpose instrument need not purchase individual instruments, especially since the price of the multipurpose instrument is less than the total price for dedicated instruments.

At present, there are many different instruments, ranging from the "dual label" instrument for luminescence and fluorescence measurements in the lowest price class, through "multilabel readers" for measuring fluorescence, luminescence and for photometry in the middle price class, to "high end" instruments for luminescence, fluorescence, photometry, fluorescence polarization, bioluminescence resonance energy transfer (BRET), fluorescence resonance energy transfer (FRET), time resolved fluorescence (TRF), and liquid scintillation counting (LSC), in the most various combinations.

Unfortunately, in designing such multipurpose instruments for the types of measurement desired, so many compromises have to be made that in the end, their performance for the various measuring methods is markedly below that of the applicable special instrument.

The primary problem in the different qualities of functions of a multipurpose instrument is the different demands in measurement technology:

For fluorescence measurements, it is essential that the specimen be projected onto the detector and that the light be passed parallel through the filters. Since the detected light comes only from the specimen that is acted upon by the excitation light source, the problem of crosstalk, that is, the interfering scattering in of light from adjacent specimens, practically does not exist. The efficiency of the light measurement, in typical fluorescence measurements, need not be very high, since the intensity of the excitation light sources can be high.

The detection sensitivity for specific fluorophores is typically limited because of the nonspecific fluorescence of solvents, organic substances, and instrument components. This nonspecific fluorescence generally has very short decay times (approximately 4 ns for proteins). Increasing the sensitivity is achieved by time resolved fluorescence. To that end, fluorescence systems with longer decay times, for instance of several hundred microseconds, have been developed. The specimen is excited with a short flash of light, for instance lasting 0.4 $\mu$s, while the detector is turned off or is passivated. Only after the nonspecific fluorescence has decayed is the detector switched to be active, and the signal is integrated for approximately 1 ms. For each specimen, this sequence is repeated cyclically, for instance a thousand times. Using filters enhances the sensitivity still further.

Another variant in fluorescence measurement is fluorescence polarization (FP). This makes use of the fact that in the very brief time between the excitation of the fluorophore and the transmission of the fluorescent radiation, the molecule rotates in space, and the polarization plane is rotated along with it. Since small (or unbonded) molecules rotate faster than large (or bonded) molecules, information about the bond order can be obtained by measuring the degree of polarization. This method does not require any separation of bonded and unbonded molecules and is therefore especially well suited for being performed in a simplified way. To determine the degree of polarization, the specimen is illuminated with linearly polarized light, and the nonrotated (parallel) and rotated (orthogonal) components in the emitted fluorescent light are measured. This is done by means of two further polarization filters (analyzers).

In luminescence measurements, conversely, in which the photons are generated by a chemical reaction, the number of photons is much less than in fluorescence. These systems must therefore be optimized, for "collecting" all the photons emitted as completely as possible and for detecting them completely. These systems normally comprise optical systems, predominantly optical waveguides, which pick up the photons directly at the specimen and carry them on to the detector. In standard luminescence measurements, it is not necessary to place filters in between.

A more recent luminescence measurement method, especially for examining cell properties, for instance of proteins, is the aforementioned BRET. For these measurements, it is necessary to provide filters (emissions filters) upstream of the detector. Most producers for BRET therefore use their fluorometers, in which emissions filters are part of the equipment anyway. As in the case of all luminescence measurements, however, in BRET as well the photon emissions are tripped by a chemical reaction, and therefore only a small number of photons are present. The sensitivity of fluorometers is therefore inadequate for high-quality BRET measurements.

Prior Art

From European Patent Disclosure EP 0 803 724 A2, a multilabel measuring instrument is known which fails to overcome the above-discussed problems, primarily because the displaceable mirror block in it, designed for all kinds of measurements, prevents high-efficiency light passage for detecting weak luminescence signals. The space angle, detected by the lens, of the light projected from the specimen is small, and so only a small proportion of the photons originally transmitted reach the detector. Moreover, in this arrangement crosstalk of specimens in adjacent specimen holders of the microtiter plate is high. This makes the results of measurement wrong, if a highly luminous specimen located next to a specimen of low luminosity is so bright that too high a value is measured at the low-luminosity specimen.

From these examples it can be seen that the requirements made of a multipurpose measuring system for optimal function are manifold. For reasons of optics, geometric size, the availability of lenses with special material and a certain index of refraction, compromises had to be made if a more or less common optical path was to be used, and the overall result of these compromises is low performance.

SUMMARY OF THE INVENTION

A first object of the invention is to create a multipurpose measuring instrument, whose measurement properties are practically not at all less than the measurement properties of corresponding individual instruments.

Another object is to create a luminescence measuring instrument that is suitable in particular for BRET measurements with high detection sensitivity as well, and which in particular can be simply expanded to make a multipurpose measuring instrument.

These objects are attained in accordance with the characteristics of claims 1 and 13.

The concept of the invention turns away from the known provision that all the functions must be measured with a fixed detector, one measurement position, a fixed excitation source, and, most important, a single optical path (measurement light path).

The invention aims at optical conditions that are optimized for every measurement function and provides the prerequisites for accommodating the required components in one housing. For every measuring function, individual detectors and beam sources can be used; the detector and the fluorescence-exciting beam source with its associated excitation filters are movable, in accordance with advantageous embodiments, and are moved by motor into the position required for each particular measurement, while the other components of the optical system are stationary.

For nearly all detection techniques, emissions filters are necessary. Because according to the invention a single filter holder (filter wheel or filter slide) that can be used for all measurements is used, with filters for the various measurement light paths, the instrument is simplified considerably. The possible measurement positions in the specimen plane are preferably located in a vertical face extending through the center points of the filters. If a filter wheel with filters disposed at equal spacing from the center point is used, the measurement positions in the specimen plane are thus located on a circular arc, while if a filter slide with linearly disposed filters is used, the measurement positions in the specimen plane are located on a straight line.

The common detector (for instance, a photomultiplier) used for the various detection modes is moved to that end along a corresponding circular arc. In the case of a filter slide as the filter holder, the detector is brought into the various filter or measurement positions by means of a linear motion.

The following measurements and combinations are examples that can be performed with the apparatus of the invention:

(1) Fluorescence from above, which can be combined with FP;

(2) Fluorescence from below;

(3) Luminescence, which can be combined with BRET;

(4) Photometry (detector below), either combined with (1) or separately;

(5) TRF, with its own measurement position, or in combination with (1) and (2).

The common filter holder proves to be especially advantageous, among other reasons, because it can also introduce a filter into the measurement light path when BRET measurements are performed with the luminescence measuring device of the instrument of the invention, which as will be explained in detail below is especially well suited to this type of measurement, because of the high detection sensitivity assured here for the emitted photons.

The common filter holder and its disposition in a horizontal plane above the specimen plane is the fundamental provision, including in the luminescence measuring device of the invention in the form of an individual measuring instrument, for a compact structure with a broad spectrum of applications, and it creates the structural prerequisites for simple expansion of the luminescence measuring device into a multipurpose measuring instrument.

BRIEF DESCRIPTION OF THE DRAWINGS

Preferred exemplary embodiments will now be described in detail in conjunction with drawings, which show:

FIG. 6: a vertical section in the plane defined by the axes A—A and B—B in FIG. 2;

FIG. 7: the detail X in FIG. 6;

DESCRIPTION OF THE PREFERRED EXEMPLARY EMBODIMENTS

Figure 1:
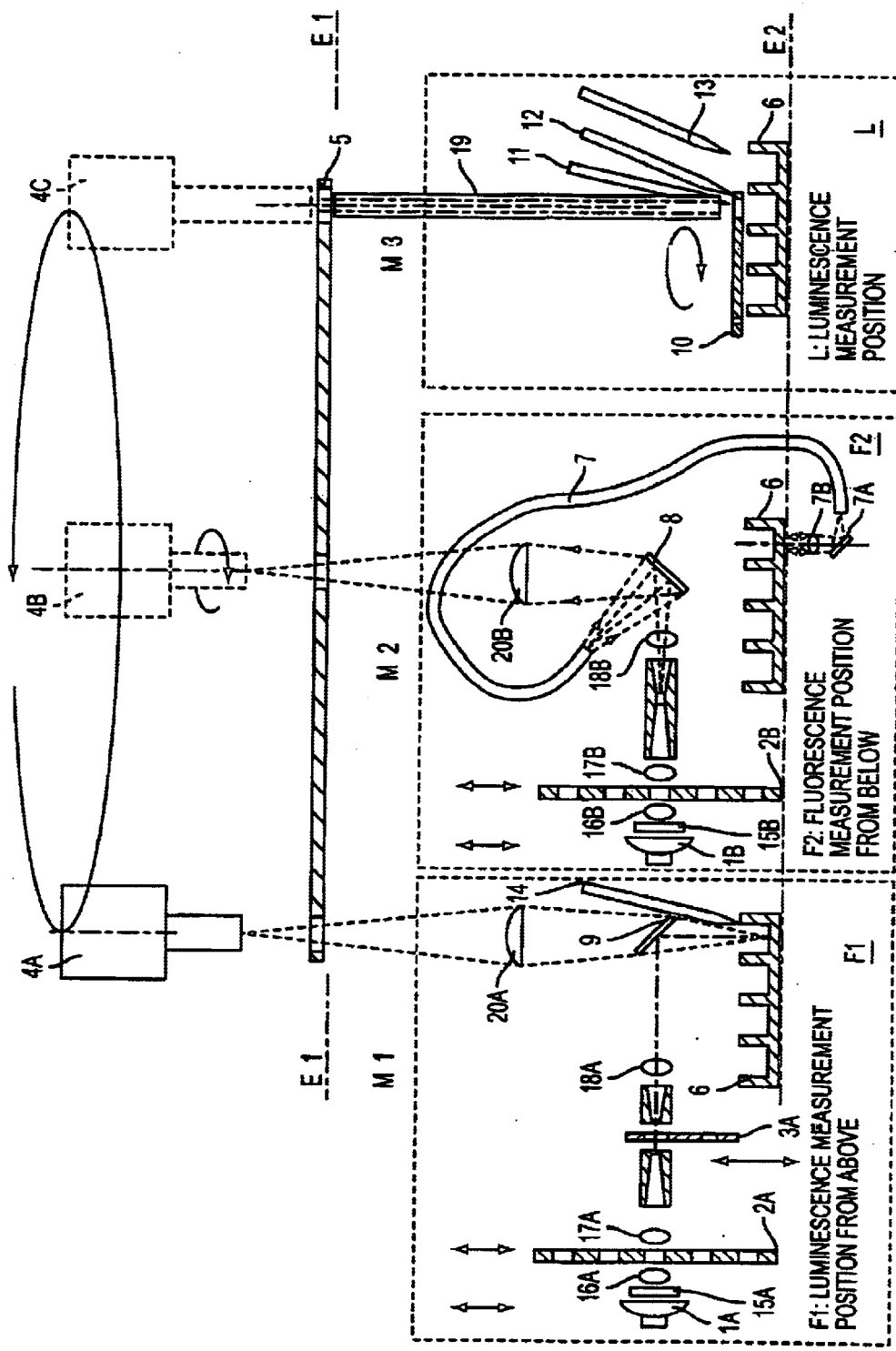
FIG. 1: a schematic illustration of the measurement light paths.

FIG. 1 is an overview of the components of the apparatus of the invention, taking as an example three measurement light paths, that is, a first measurement light path M1 with a first fluorescence measuring device F1 for a measuring fluorescence from above, a second measurement light path M2 with a second fluorescence measuring device F2 for measuring fluorescence from below, and a third measurement light path M3 with a luminescence measuring device L for measuring luminescence with or without filters. In all three measurements, the specimen holders, which are shown schematically as indentations in a microtiter plate 6, are located in a common specimen plane E2, which as a rule is embodied by a holder plate for the microtiter plates 6 which is displaceable horizontally by means of a motor system, not shown. Still other specimen carriers are also possible, such as membranes in which the specimens emit photons. The transport mechanism of the microtiter plate successively puts the specimen holders, with the specimens to be measured, in the measurement position.

Above the specimen plane E2 and parallel to it, there is a filter holder in a horizontal plane E1, which has through openings, each filter holder being equipped with emissions filters that are required depending on the type of measurement involved. Depending on the application, these filters can be interference filters, colored glass filters, or film filters. By means of the emissions filters, the spectral range of the light passing through to the detector 4 is selected.

Located above these openings are detectors 4A, 4B, 4C. The filter holder is displaceable or rotatable in such a way that each of its openings can be associated with a corresponding filter of each of the detectors. In a preferred embodiment of the invention, the detectors 4A, 4B, 4C are embodied by one common displaceable or pivotable detector 4. In the exemplary embodiment shown, the filter holder is embodied as a filter wheel 5, with N openings spaced apart equally from the center point and at an equal angular spacing, for holding the emissions filters.

It is especially important that because of the disposition of the filter wheel in a horizontal plane E1 spaced apart from the specimen plane E2, space is created for measuring devices with mutually independent measurement light paths M1, M2 and M3. The measurement light paths M1, M2, M3 and at the detector or detectors, with the interposition of the filter wheel 5.

As a result of the construction according to the invention, the filter wheel 5 is thus used for both the luminescence measuring device L and the two fluorescence measuring devices F1 and F2. This is made possible by the provision that the measurement light paths of the three measuring devices terminate at the same radius as the filters. The same is correspondingly true for an alternate version of the filter holder as a linear slide; in that case, the various measurement light paths terminate at a straight line.

The measurement light paths schematically shown in FIG. 1, with their associated measuring devices, will now be briefly described individually:

In the first measurement light path M1 with the first fluorescence measuring device F1 for measuring fluorescence from above, the undesired infrared radiation in the light transmitted from a first light source 1A is first absorbed by means of a heat protection filter 15A. By means of an arrangement of lenses 16A and 17A and an excitation filter 2A, the wavelength is selected for exciting the fluorescence. With a displaceable aperture plate 3A, the diameter of the lighting beam can be selected to suit the format of the microtiter plate 6. A lens 18A focuses the excitation light for illuminating the specimen holder to be measured in the microtiter plate 6. By means of a partially transparent mirror 9, the light to the specimen is deflected inside the aforementioned specimen holder. The fluorescent light transmitted from the specimen to be measured is focused with a lens 20A and aimed through an opening of the filter wheel 5 at the detector 4A. By means of the filter wheel 5, the selection of filter for the particular emissions wavelength is made. For specific measurements, an injection tip 14 can be provided, with which a liquid can be introduced into the specimen holders of the microtiter plate 6.

In the second measurement light path M2 having the second fluorescence measuring device F2 for measuring fluorescence from below, the excitation light generated by a second light source 1B and a corresponding heat protection filter 15B, excitation filter 2B and lenses 16B, 17B and 18B are coupled into an optical waveguide 7 via a deflection mirror 8. The deflection mirror 8 has the appropriate angular position for the purpose in its central part. From the optical waveguide 7, the emerging excitation light passes by means of a deflection mirror 7A and a lens 7B to the bottom of the specimen holder to be measured in the microtiter plate 6. The fluorescent light transmitted from the specimen is directed back through the optical waveguide 7 to the deflection mirror 8, and from its peripheral regions, which have the appropriate angle of inclination, it reaches the detector 4B by means of a lens 20B through an opening in the filter wheel 5.

In the third measurement light path M3 with the luminescence measuring device L, an adaptation to the particular format of the microtiter plate 6 is made by means of an aperture wheel 10. The aperture wheel 10 located above the specimen plane E2 has a plurality of openings, which are steered into the desired position by a motor in such a way that the selected aperture opening is approximately equivalent to the exit opening from a specimen holder.

For transmitting the photons from the microtiter plate 6 to the photodetector 4, an optical waveguide 19 that has a larger diameter than the aperture is used, so that the photons passing from the specimen through the aperture can be detected as completely as possible. For that purpose, either one solid optical waveguide can be used, or an arrangement of individual fibers, such as a sheaf of 1-millimeter fibers. By means of injectors 11, 12, 13, the reagent that excites the luminescence is placed in the specimen holders of the microtiter plate 6. The luminescent radiation then reaches the detector 4C via the optical waveguide 19 through an opening in the filter wheel 5. In standard applications for luminescence measurement, no filter needs to be used in this opening of the filter wheel 5, but in BRET applications, suitable filters must be put into position successively.

The construction of all the measuring devices is accordingly done in such a way that the spacing between the microtiter plate and the filter wheel is always the same. As a result, the microtiter plate, filter wheel and detector are located in three parallel planes one above the other, which makes for an embodiment that is especially economical and especially efficient in terms of measurement.

Figure 2:
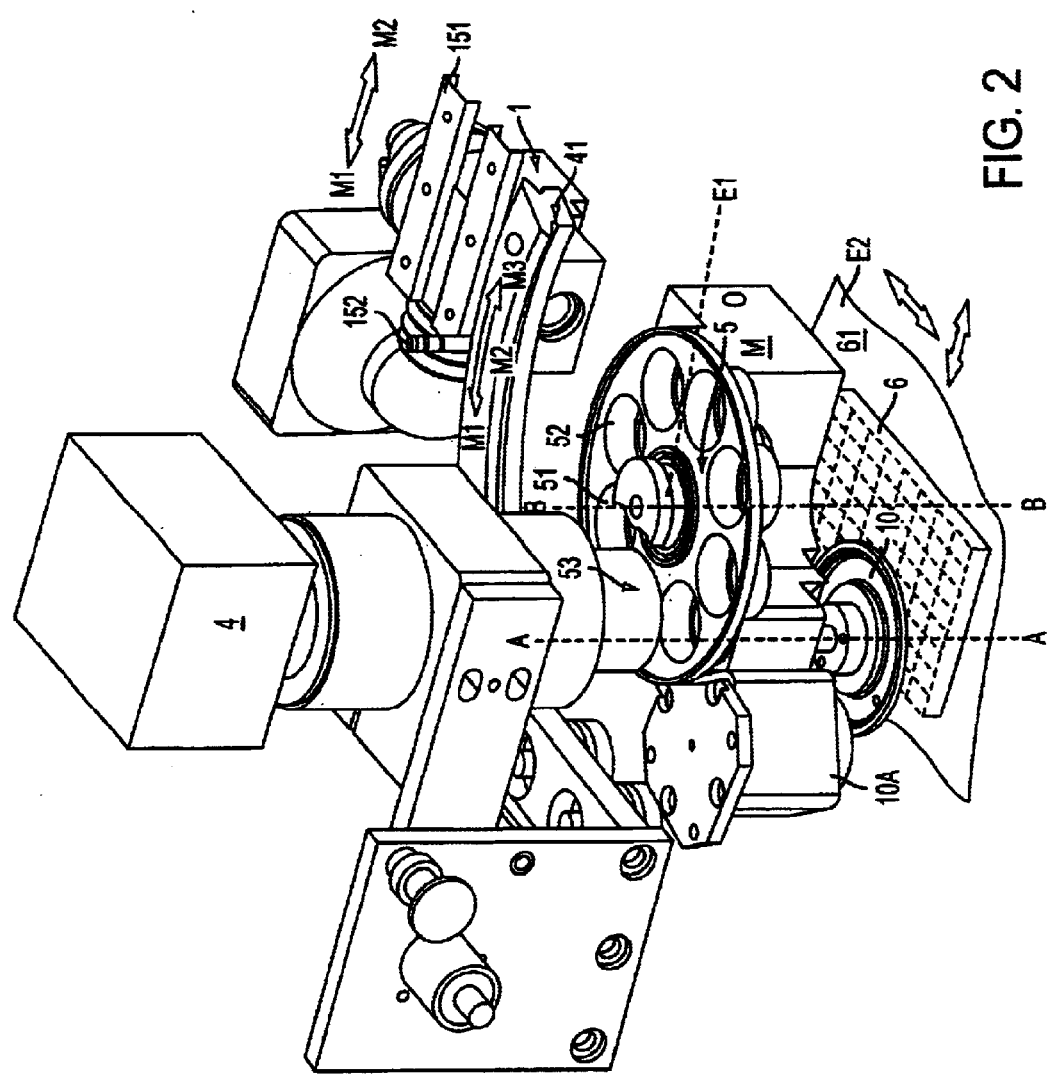
FIG. 2: a perspective view of the essential components.

FIG. 2 shows the essential components of the arrangement described above in their three-dimensional relationship, initially without describing the purely mechanical assembly and mounting devices.

On a horizontally and vertically displaceable holder plate 61, which defines the plane E2, the microtiter plate 6 with the specimen holders is moveable under the apparatus in such a way that the particular specimen to be evaluated by means of a particular measurement is placed in the measurement light path intended for that measurement. The various measurement positions as a rule differ; the measurement positions for measuring fluorescence from above and for measuring fluorescence from below can, however, fundamentally also be identical, since the two measurement light paths M1 and M2 originating at the specimen holder do not overlap.

In the horizontal plane E1, the filter wheel 5 is supported rotatably about a vertical axis. The electric motor 10A rotates the filter wheel 5 via a gear wheel engagement, until the opening with the desired filter is located in the measurement light path; this makes fast, automatic filter changing possible.

In the exemplary embodiment shown, the spacing of the measurement light paths M1, M2, M3 is equivalent to the spacing of the filters, since a "standard filter" can then be associated with each measuring method, making it unnecessary to change filters upon a change in the measuring method as often.

In the exemplary embodiment shown, the filter wheel 5 has eight openings 51 . . . 58, which can be occupied selectively with suitable emissions filters (not shown in FIG. 2). Above the filter wheel 5, one common radiation detector 4 (instead of the equally possible separate detectors 4A . . . 4C in FIG. 1) is retained movably on a circular-arc rail 41 in such a way that its inlet opening is movable over a circular arc above the filter wheel 5; along this circular arc, it can assume the three measurement positions sketched in FIG. 1, as terminal points of the respective three measurement light paths M1, M2, M3. The radius of the circular arc that the center point of the inlet opening of the detector 4 describes in the process is equivalent to the radius of the circle extending through the center points of the openings 51 . . . 58, so that in this way it is possible for each of the openings 51 . . . 58 with the specifically provided filters to be associated with each of the measurement positions of the detector 4.

In an advantageous feature of the invention, the two light sources 1A and 1B are embodied by a common light source 1 (FIG. 2), which is retained displaceably or rotatably between the starting points of the measurement light paths M1 and M2. In the embodiment shown, the module comprising the light source 1, heat protection filter 15 and first lens 16A, 16B is supported displaceably by means of a linear guide 151. By means of a spring 152, it is put into one of the two positions. By means of a detector mount secured on a circular guide, the module is automatically moved as well upon movement into the second fluorescence measuring position and is then located at the point necessary for coupling in the excitation light.

The fluorescence measurement light paths M1 and M2 are predetermined in their three-dimensional relationship and disposition by the components shown in FIG. 1, which are accommodated in the measurement block M. Thus the components 2A/2B, 3A, 15A/15B, the two mirror arrays 8 and 9, one end of the optical waveguide 7, and the two "exit lenses" 20A and 20B are all located in the measurement block M. The position of the lenses 16A/16B and 20A/20B thus defines the input-side and output-side "spacing" of the measurement light paths M1 and M2 in the measurement block M; the input-side spacing is equivalent to the travel distance of the lamp 1 on the linear guide 151, while the output-side spacing is the movement travel of the detector 4 on the arc rail 41, as can also be seen from FIG. 1.

In the exemplary embodiment shown in FIG. 2, the detector 4 is in the luminescence measuring position, that is, is located at the end of the third measurement light path M3, which extends from the microtiter plate 6 via the optical waveguide through one of the openings 51 . . . 58 in the filter wheel 5 to the detector 4.

The disposition of the measurement light paths is arbitrary, however, to the extent that they can be essentially predetermined by the disposition of the components in the measurement block M and by the course of the optical waveguide 7 or also the course of the optical waveguide 19; however, in every case, all the measurement light paths terminate at the circle defined by the center points of the openings 51 . . . 58.

Basically, the apparatus of the invention as shown in FIGS. 1 and 2 has its own measuring device for each measurement light path, the measuring device being optimized for the particular measurement method and having individual beam optics, as needed; only those components that are optimally suited or optimizable for the particular measurement mode are used in common (lamp 1, detector 4, filter wheel 5), making a compact design of the entire arrangement possible without having to do without the measurement quality of three individual instruments.

Figure 3:
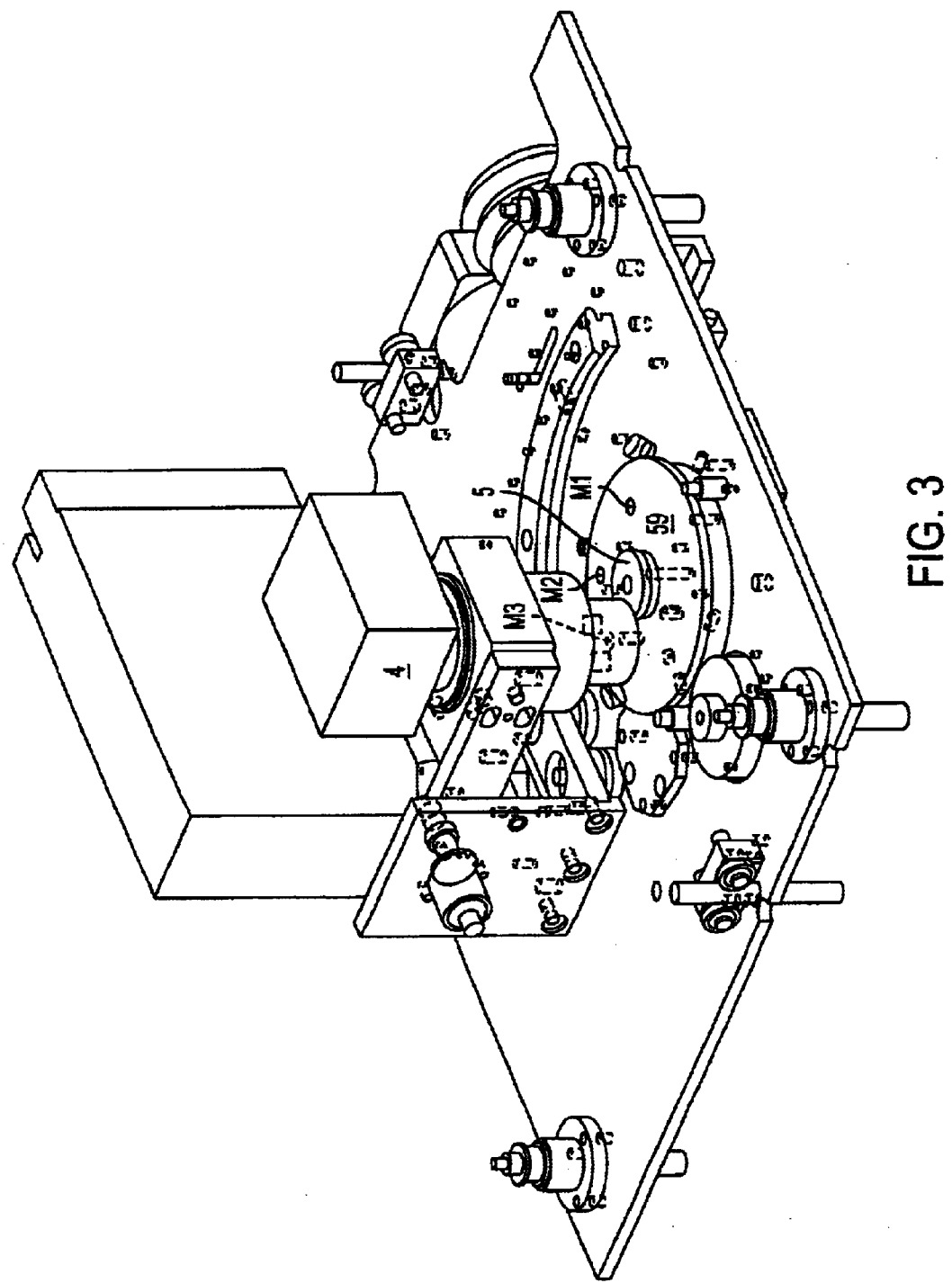
FIG. 3: a first perspective view from above of the entire apparatus.
Figure 4:
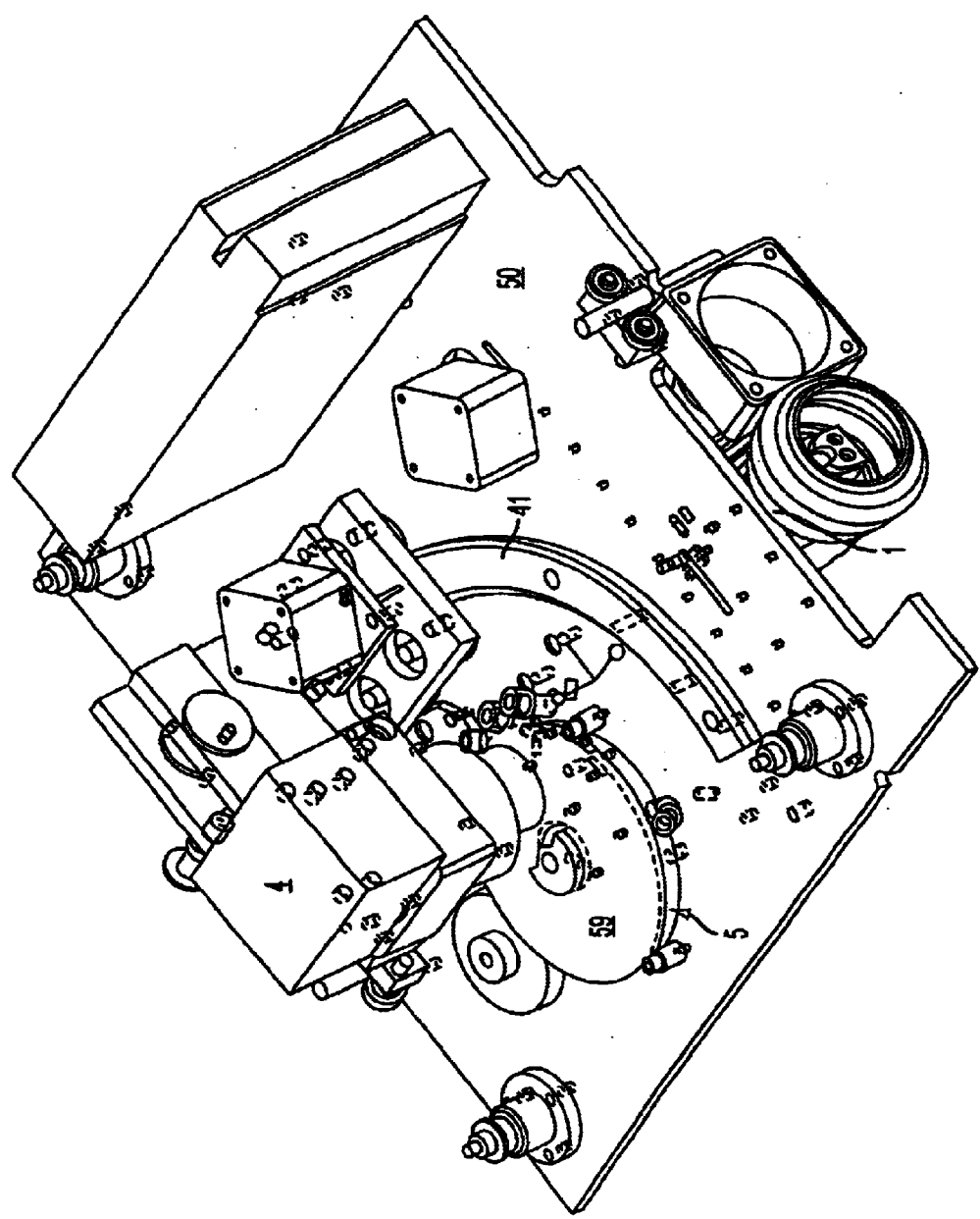
FIG. 4: a second perspective view from above of the entire apparatus.
Figure 5:
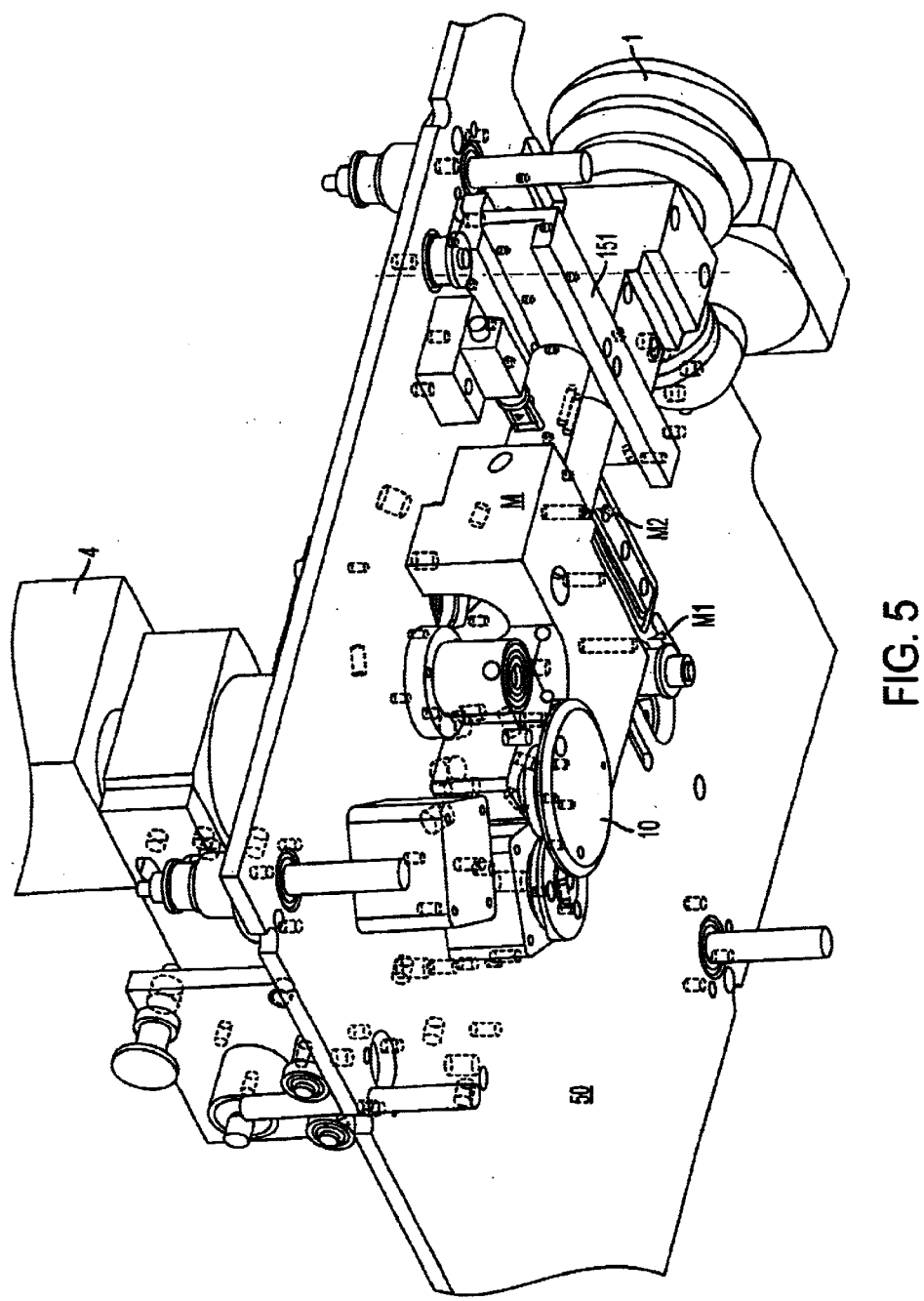
FIG. 5: a perspective view from below of the entire apparatus.

FIGS. 3–5 show further structural design characteristics for converting the apparatus of the invention into a concrete instrument; this involves in particular a carrier plate 50, on which the above-described components are mounted. By means of a covering 59 above the filter holder with an opening for the active measurement light path to the detector 4, stray light from an adjacent measurement path is prevented from being able to reach the detector. It is supported jointly with the filter wheel 5 and is moved with it by the detector in such a way that the opening is located above the particular active measurement light path.

If, in the further concept of the invention, a luminescence instrument is to be made as a stand-alone instrument, then its overall structure corresponds to the structure shown in FIGS. 2–5, but without the components that are needed for the fluorescence measurements, and so a detailed description of the overall structure of a such a luminescence instrument will not be provided here.

Figure 8:
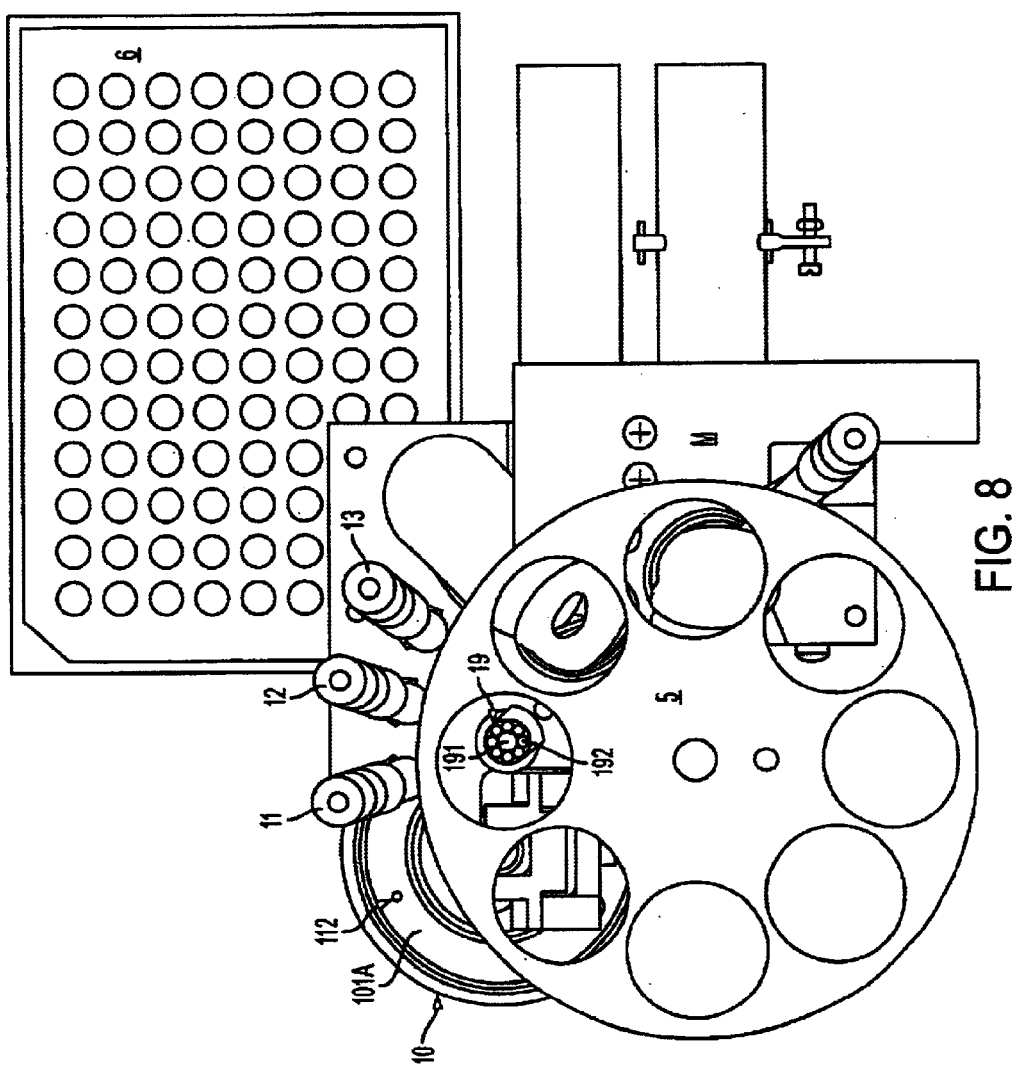
FIG. 8: a fragmentary view from above of the arrangement of FIG. 6.
Figure 9:
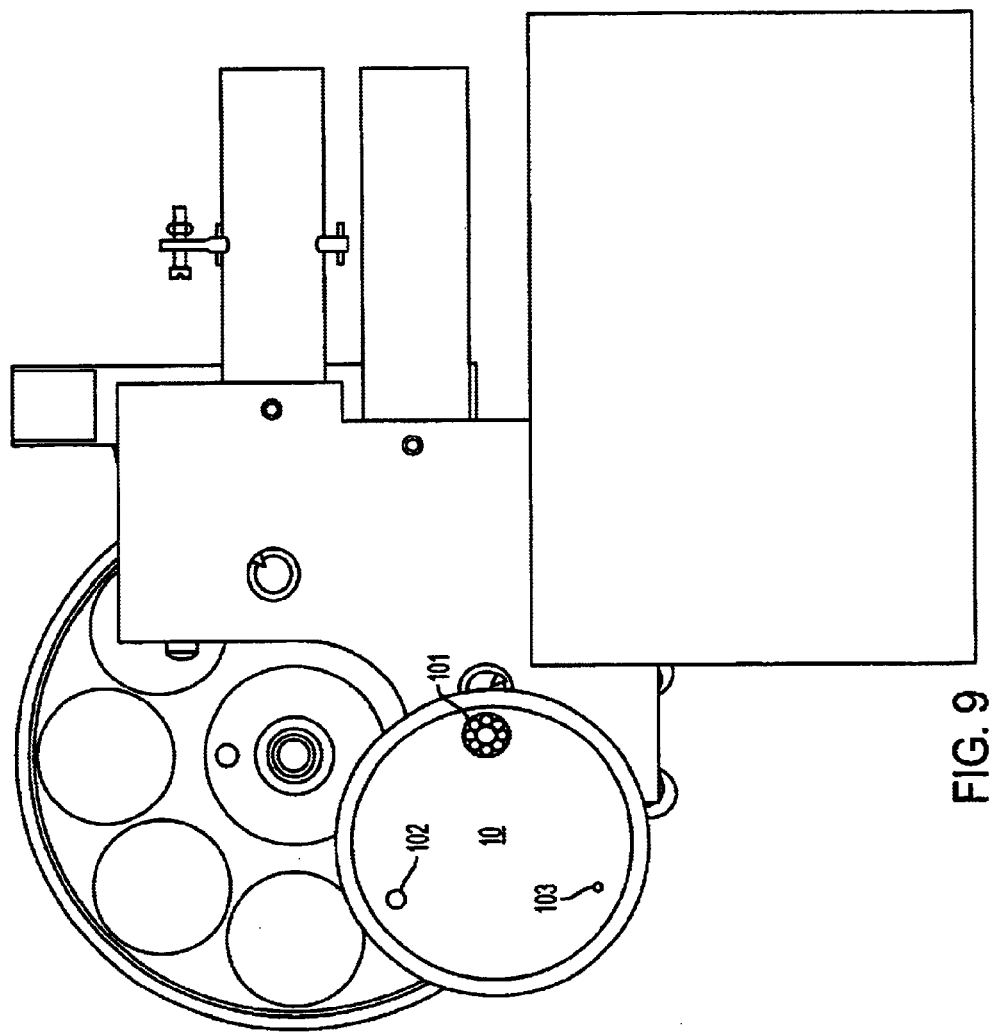
FIG. 9: a fragmentary view from below of the arrangement of FIG. 6.
Figure 10:
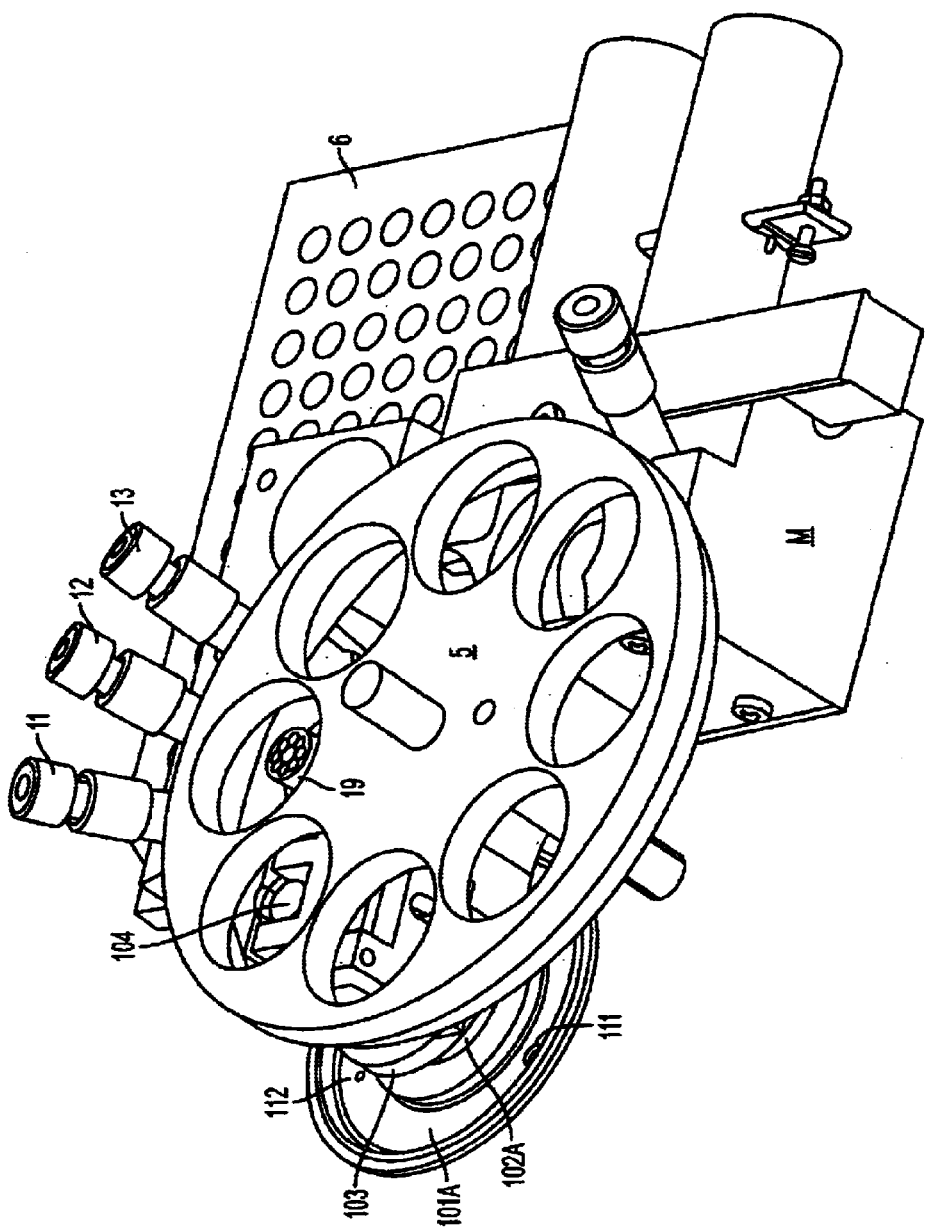
FIG. 10: a perspective view from above of the arrangement of FIG. 6.
Figure 11:
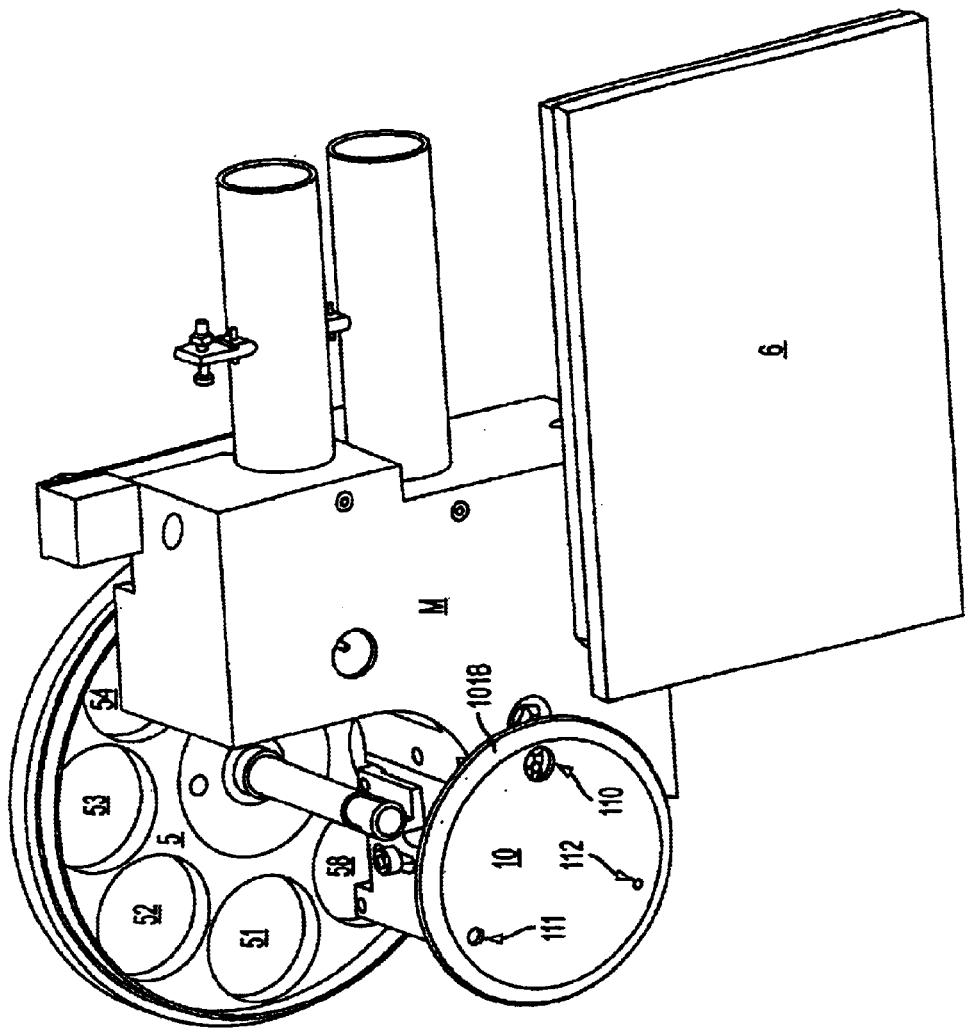
FIG. 11: a perspective view from below of the arrangement of FIG. 6.
Figure 12:
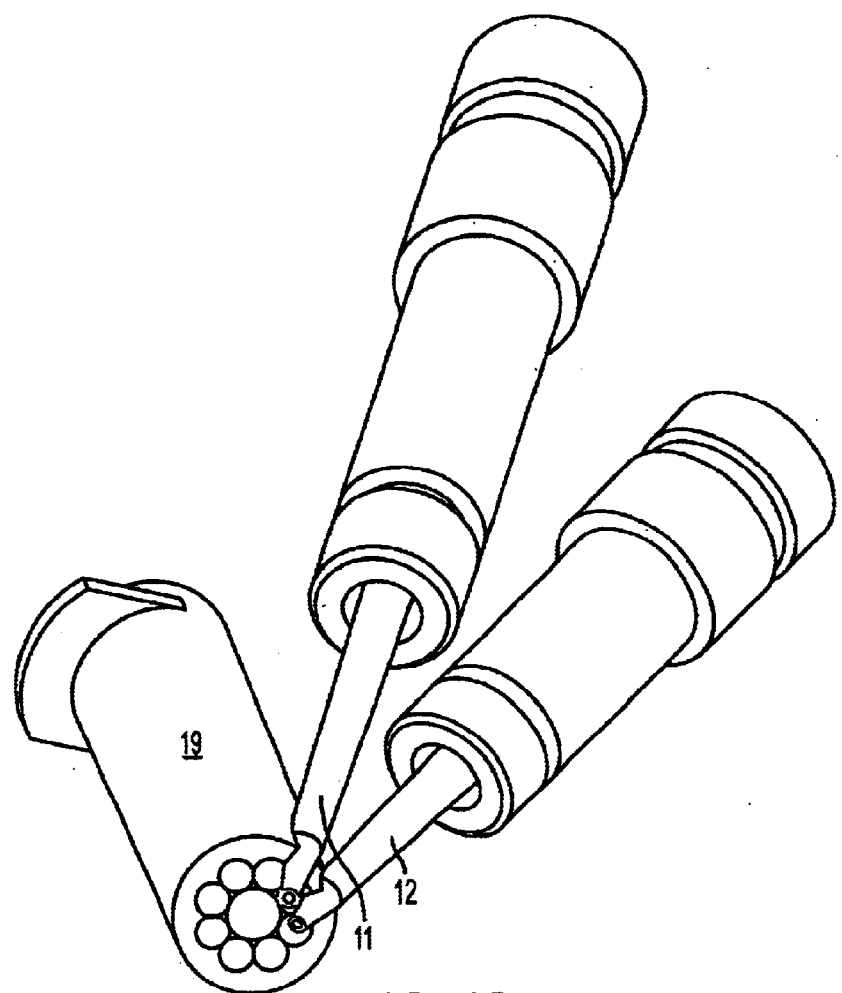
FIG. 12: a perspective view of the optical waveguide.
Figure 13:
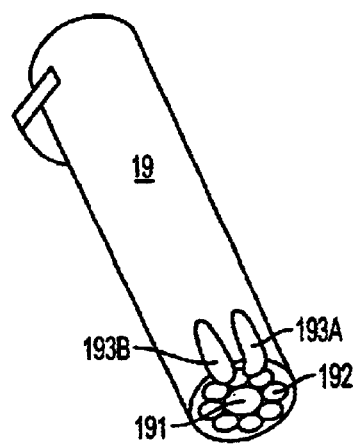
FIG. 13: the optical waveguide of FIG. 12 with injectors inserted.
Figure 14:
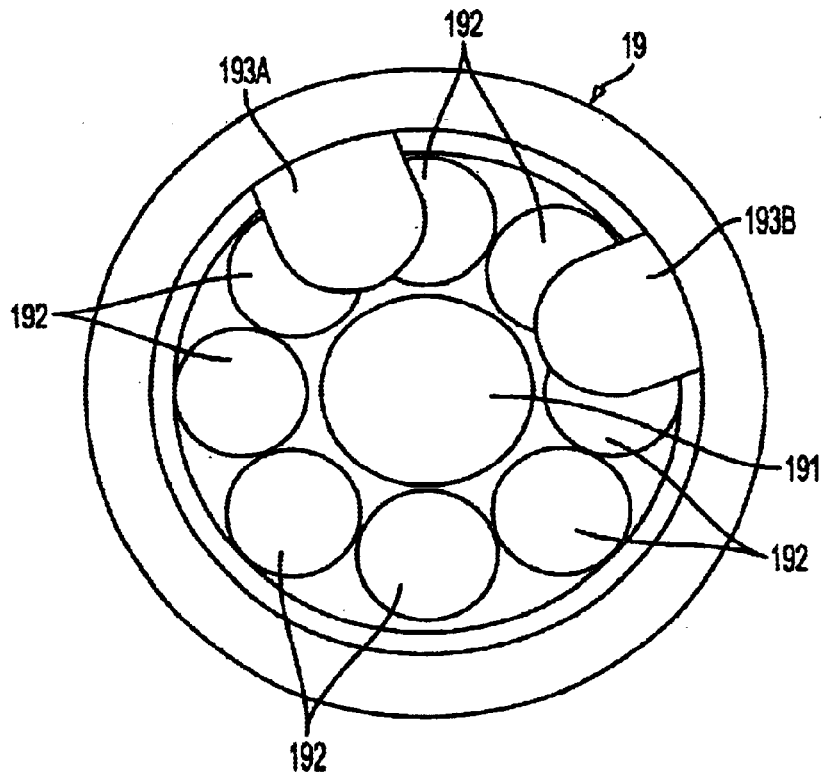
FIG. 14: a view of the optical waveguide from below.

The structural design of the luminescence measurement is particularly important, because it is also suitable for luminescence measurements of the kind that require at least one filter. A particularly preferred embodiment of the luminescence measurement, in the context both of the above-described multipurpose measuring instrument and of a luminescence measuring instrument as an individual instrument, will now be described in further detail in conjunction with FIGS. 6–8, with reference to the luminescence measuring device L:

The essential components of the luminescence measuring device L are also mounted and associated with one another in the measurement block M that is disposed between the microtiter plate 6 and the filter wheel 5. The specimens to be measured are located in the measurement containers (indentations) in the microtiter plate 6.

The measurement block M has three vertical bores: one bore B10 for the aperture wheel 10, one bore B19 for the optical waveguide 19, and one bore B5, which is split into two parts.

Figure 16:
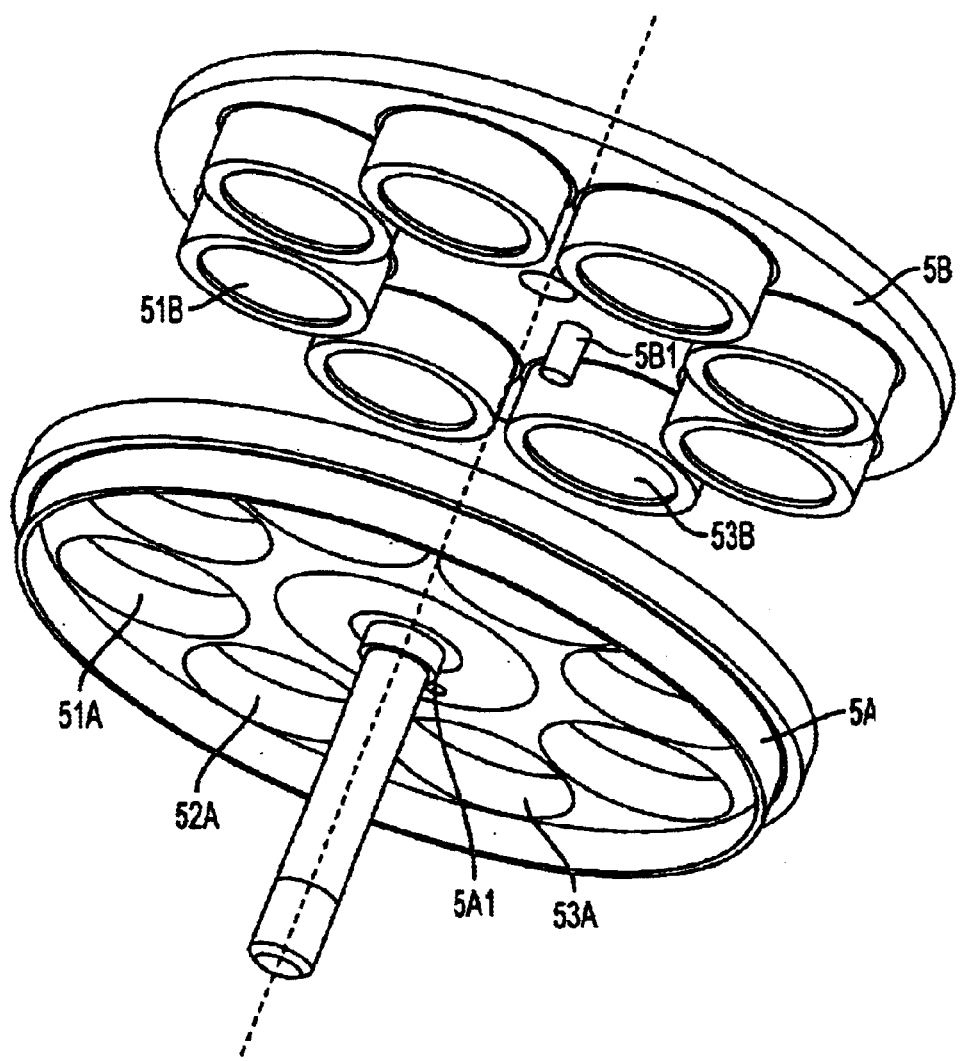
FIG. 16: a detail of the filter wheel.

A preferred embodiment of the filter wheel 5 is shown in FIG. 16:

The filter wheel 5 comprises a lower part 5A as a holder part, with openings 51A . . . 58A, which part is inserted into the bore B5 in the measurement block M, and an upper 5B, with cylindrical receptacles 51B . . . 58B for holding emissions filters IF. The two parts 5A and 5B are placed one in the other in such a way that the receptacles 51B . . . engage the respective openings 51A . . . (FIG. 6); a coding pin 5B1 engages a recess 5A1 in the lower part, thus assuring an unambiguous association of the receptacles 51B . . . with the openings 51A . . . .

This embodiment makes it considerably simpler to convert the apparatus to a different set of emissions filters, especially on a change of measuring method, since the entire filter wheel 5 need not be removed from the measurement block M; instead (once the requisite space has been opened up, for instance by pivoting the detector 4 out of the way), the upper part 5B merely needs to be removed and replaced. Expediently, for that purpose a plurality of sets of upper parts 5B with a particular disposition of emissions filters can be kept in readiness for the sake of fast replacement.

Figure 15:
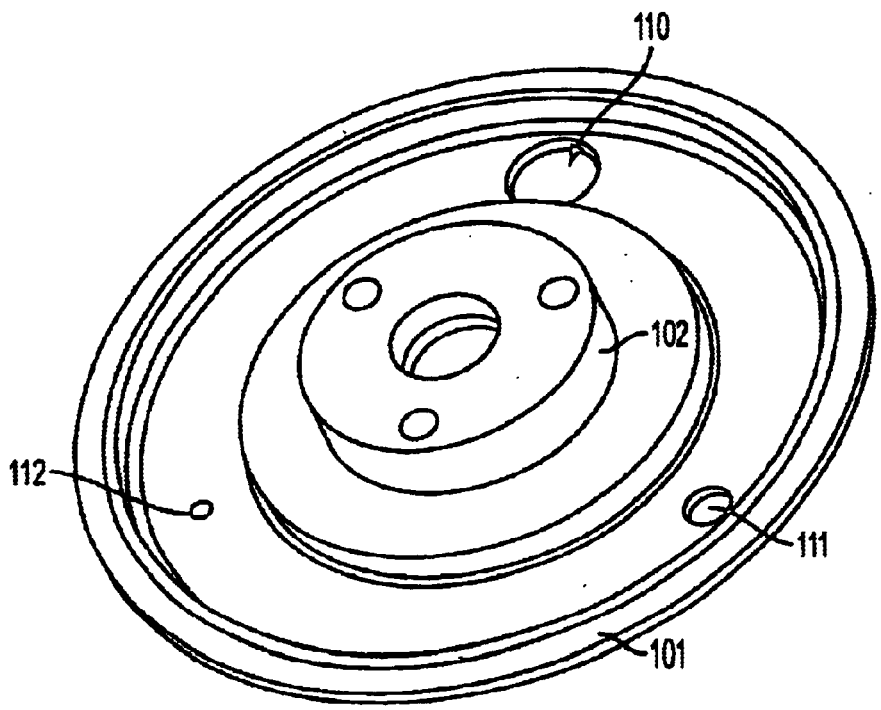
FIG. 15: a fragmentary perspective view of the aperture wheel.

The aperture wheel 10 is essentially a body generated by rotation, with four segments of different radii, and this body can be produced either as a one-piece plastic molded part or in the form of a plurality of cylindrical bodies that are joined together; FIG. 15 shows one such part of the aperture wheel.

The first, lowermost segment 101 with the greatest radius includes the actual apertures, in the form of openings 110, 111, 112 of different diameters, in an annular groove 101A. To enable adaptation to the various diameters of the measurement containers/indentations of different microtiter plates, different aperture openings can be positioned between the measurement container and the optical waveguide. The center points of the three openings 110, 111, 112 shown (the total number could be as high as eight, for instance) are all located at the same radius about the axis X—X of the aperture wheel 10. For instance, the diameters of the aperture openings 110, 111, 112 are selected to be 6.0 mm, 3.0 mm and 1.5 mm, for specimen holders in the form of respective microtiter plates with 96, 384, and 1536 indentations each.

The second segment 102 of the aperture wheel 10 has a shorter radius than the first segment 101, while the third segment 103 located farther upward in turn has a larger radius, forming an encompassing groove 102A.

Finally, the fourth segment 104 adjoins the others at the top and extends nearly to the top of the measurement block M and serves essentially to provide secure vertical guidance of the aperture wheel 10, but still allows its vertical displacement to a slight extent.

Laterally of the measurement block M is a motor 20, which has a gear wheel 21 that meshes with teeth provided on the circumference of the third segment 103 of the aperture wheel 10, so that upon an activation of the motor 20, a rotation of the aperture wheel 10 can be controlled about an angle such that one of the aperture openings 110, 111 or 112 is located exactly in the measurement position above the outlet opening of an indentation in the microtiter plate 6 having the specimen to be measured, when this specimen is moved underneath and past the aperture plate 10. This makes a fast change of aperture possible upon a change of type of the microtiter plate 6.

Located below the gear wheel 21 is a disk 22, which meshes with the groove 102A; the heights of the disk 22, groove 102, gear wheel 22 and third segment 103 are dimensioned such that a vertical motion of the aperture wheel 10 between two terminal positions is possible while maintaining the tooth engagement.

This assures on the one hand that the aperture wheel 10 cannot fall out of the measurement block M if there is no microtiter plate 6 located beneath it, but an automatic height adaptation is also attained, in the sense that even if there are dimensional tolerances in the height of the exit openings in the specimen holders in the measurement position of the microtiter plate 6, the aperture wheel 10 rests by its own weight on the microtiter plate 6, so that no gap can form between the microtiter plate 6 and the aperture wheel 10, and crosstalk effects are thus reliably avoided.

The bottom edge of the first segment 101 is beveled in the form of a ramp 101B, so that it is automatically lifted out of its lower terminal position (in which there is no microtiter plate in the measurement position) to the current measurement level upon insertion of a microtiter plate.

The lower end of the optical waveguide 19 protrudes with scarcely any play (0.1 to 0.2 mm) into the groove 101A of the first segment 101, so that the opposed faces of the optical waveguide end, segment 101 and measurement block M form an optical labyrinth, so that once again no scattered light effects can occur.

The optical waveguide can be embodied as a cylindrical block of transparent plexiglass, glass, or quartz, for instance, and the cylinder wall can be provided with reflective material, such as titanium oxide or metallizing. The particularly preferred embodiment, shown, of the optical waveguide 19 is a combination of individual optical waveguide fibers 191, 192 into a sheaf, from which a rigid, dimensionally stable optical module is produced by being potted with plastic material. Since the light does not exit the measurement container parallel upward but rather in random fashion, optical waveguide fibers are used that cause the light to enter at an entrance cone or entrance angle that is not too small, for the sake of achieving the highest possible photon yield. Since the entrance angle also determines the exit angle from the optical waveguide 19, a maximum value must on the other hand not be exceeded, so that the beams of light emerging from the upper end of the optical waveguide 19 will not exceed a maximum divergence, because that would impair the function of the interference filters IF (FIG. 6) in the filter wheel 5, which filters function best when the beams of light strike the filter vertically. An optimal compromise in this respect has proved to be of value for the entrance angle of approximately 15° from the optical axis.

To achieve this compromise, in the preferred exemplary embodiment the optical waveguide 19 comprises one central fiber 191, with a diameter of 3 mm, and eight fibers 192, each with a diameter of 2 mm.

Two recesses 193A, 193B on the lower edge of the optical waveguide 19 serve to hold the injection tips 11 and 12 for adding reagents to the specimen, either before, during or after the measurement. As a result, two reagents can be injected through the selected aperture opening 110, 111, 112 into the specimen located in the measurement position, and the luminescence reaction tripped as a result can be measured without delay. One or more further injectors 13 can inject into measurement containers located outside the measurement position.

The light exiting from the upper end of the optical waveguide 19 passes through one of the openings 51 . . . 58 of the filter wheel 5 before striking the detector 4, where it is measured. Depending on the type of luminescence measurement to be performed, either at least one suitable filter IF (or two filters in the case of BRET measurements, for instance), or no filter, for conventional luminescence measurements, is located in the openings.

The luminescence measuring device of the invention described above is especially well suited for inclusion as a multilabel reader into the apparatus. However, the embodiment of the luminescence measuring device also make the instrument especially suitable as a stand-alone instrument for BRET measurements.

The instrument of the invention thus covers a wide range of uses; it can be equipped either completely or selectively with individual measuring devices, whose measurement light paths need merely terminate at a position that is reachable by the filters of the common filter holder; however, it can also optionally be retrofitted later.

What is claimed is:

1. An apparatus for selective measurement of luminescent and/or fluorescent radiation, in particular, from specimen holders via at least two measurement light paths by means of at least two measuring devices, wherein the apparatus comprises at least one beam source and at least one detector, characterized in that a single filter holder, retained rotatably or displaceably in a horizontal plane (E1), is provided, which has at least two openings, each for holding one emissions filter as needed; that the specimen holders are displaceable in a common specimen plane (E2) below the horizontal plane (E1) and parallel thereto into their measurement positions; and that the measuring devices (F1, F2, L) are disposed essentially between the two planes (E1, E2) in such a way that each of their associated measurement light paths (M1, M2, M3) can extend through each opening in the filter holder, the opening being selectable by rotation or displacement of the filter holder, to said at least one detector.

2. The apparatus of claim 1, characterized in that the measurement light paths (M1, M2, M3) extend, spaced apart from one another, through the horizontal plane (E1) of the filter holder.

3. The apparatus of claim 2, characterized in that the filter holder is a filter wheel (5), with N openings (51 . . . 58), disposed at equal spacing from the center point and at an equal angular spacing.

4. The apparatus of claim 3, characterized in that the spacing of the measurement light paths (M1, M2, M3) on passing through the filter wheel (5), or its horizontal plane (E1), is equivalent to the spacing of the center points of the openings (51 . . . 58) of the filter wheel (5).

5. The apparatus of claim 4, characterized in that said at least one detector is a common detector that is guided over a circular arc across the openings (51, 52, 53) in the filter wheel (5) that are used by the measurement light paths (M1, M2, M3).

6. The apparatus of claim 2, characterized in that the measurement positions of the specimen holders on the specimen plane (E2) are located on a curve that extends at a vertical face which is defined by the center points of the filters of the filter holder.

7. The apparatus of claim 1, characterized in that said at least one detector is a common detector (4) which is movable above the filter wheel (5) to the measurement light paths (M1, M2, M3).

8. The apparatus of claim 1, characterized in that at least two measurement light paths (M1, M2) are provided with fluorescence measuring devices (F1, F2), into which the radiation from said at least one beam source is coupled in order to excite fluorescence.

9. The apparatus of claim 8, characterized in that for a measurement of fluorescence from above, the first fluorescence measuring device (F1) contains a first mirror array (9), from which the exciting radiation of a lamp (1A) of said at least one beam source reaches the top side of the specimen holders.

10. The apparatus of claim 8, characterized in that for a measurement of fluorescence from below, the second fluorescence measuring device (F2) contains a second mirror array (8), from which the exciting radiation of a lamp (1B) of said at least one beam source reaches the underside of the specimen holders via an optical waveguide (7) and returns to the mirror array (8).

11. The apparatus of claim 10, characterized in that the fluorescence measuring devices (F1, F2) contain a common lamp (1) as said at least one beam source, which is movable to the measurement light paths (M1, M2).

12. The apparatus of claim 1, characterized in that a third measurement light path (M3) is provided with a luminescence measuring device (L).

13. The apparatus of claim 12, characterized in that in the luminescence measuring device (L), an aperture wheel (10) with a plurality of openings (110, 111, 112) of various diameters is retained immediately above the specimen holders.

14. The apparatus of claim 13, characterized in that the aperture wheel (10) is vertically displaceable and rests sealingly, in the measurement position, on the specimen holders.

15. The apparatus of claim 12, characterized by an optical waveguide (19) extending essentially from the top side of an aperture wheel (10) to the underside of the filter holder.

16. The apparatus of claim 15, characterized in that the optical waveguide (19) is formed of a rectilinearly extending sheaf of optical waveguide fibers (191, 192).

17. The apparatus of claim 16, characterized in that the optical waveguide fibers used have an entrance cone for light with an opening angle of approximately ±15°.

* * * * *